United States Patent [19]
Duncan et al.

[11] Patent Number: 5,501,637
[45] Date of Patent: Mar. 26, 1996

[54] TEMPERATURE SENSOR AND METHOD

[75] Inventors: Walter M. Duncan; Francis G. Celii, both of Dallas; Steven A. Henck; Ajit P. Paranjpe, both of Plano; Douglas L. Mahlum, Allen; Larry A. Taylor, N. Richland Hills, all of Tex.

[73] Assignee: Texas Instruments Incorporated, Dallas, Tex.

[21] Appl. No.: 309,347

[22] Filed: Sep. 20, 1994

Related U.S. Application Data

[63] Continuation of Ser. No. 104,963, Aug. 10, 1993, abandoned.

[51] Int. Cl.$^6$ .................. G01J 5/10; G01J 5/58; G01J 4/04; G02F 1/01
[52] U.S. Cl. ............... 374/126; 374/128; 374/9; 250/225; 356/367; 356/369
[58] Field of Search .................. 374/126, 128, 374/9; 250/225; 356/364, 367, 368, 369

[56] References Cited

U.S. PATENT DOCUMENTS

| | | | |
|---|---|---|---|
| 3,796,099 | 3/1974 | Shimotsuma et al. | 374/126 |
| 4,919,542 | 4/1990 | Nulman et al. | 374/128 |
| 4,956,538 | 9/1990 | Moslehi | 374/126 |
| 4,979,133 | 12/1990 | Arima et al. | 374/126 |
| 5,011,295 | 4/1991 | Krishnan et al. | 374/126 |
| 5,131,752 | 7/1992 | Yu et al. | 356/369 |
| 5,165,796 | 11/1992 | Gat et al. | 374/128 |

FOREIGN PATENT DOCUMENTS

| | | | |
|---|---|---|---|
| 0121123 | 9/1980 | Japan | 374/128 |
| 0122924 | 9/1981 | Japan | 374/128 |
| 2082767 | 3/1982 | United Kingdom | 374/128 |

Primary Examiner—Diego F. F. Gutierrez
Attorney, Agent, or Firm—W. Daniel Swayze, Jr.; W. James Brady, III; Richard L. Donaldson

[57] ABSTRACT

A direct, noncontact temperature sensor includes an ellipsometer (104–106) to determine absorptance for layered structures and a pyrometer (102) to determine emissive power and combines the two measurements to determine temperature.

15 Claims, 2 Drawing Sheets

TEMPERATURE SENSOR AND METHOD

This application is a continuation of application Ser. No. 08/104,963, filed Aug. 10, 1993, now abandoned.

CROSS-REFERENCE TO OTHER APPLICATIONS

Coassigned pending U.S. patent application Ser. No. 07/890,511, filed May 28, 1992, discloses related subject matter and is hereby incorporated by reference.

BACKGROUND OF THE INVENTION

The invention relates to electronic devices, and, more particularly, to electronic temperature sensors and methods of temperature sensing.

Many manufacturing processes, such as integrated circuit fabrication, require accurate temperature sensing in real time as part of process control. Indeed, in integrated circuit fabrication, thermally activated steps demand precise wafer temperature control. The current trend in integrated circuit fabrication to single wafer processing instead of batch processing permits in situ individual wafer temperature monitoring. However, such wafer temperature monitoring should be by a direct but noncontact approach.

Current integrated circuit fabrication generally employs thermocouples contacting the backside of a wafer for temperature sensing. However, poor contact implies a loss of accuracy. Furthermore, the frontside surface temperature determines processing behavior, not the wafer backside surface temperature. But frontside contact leads to surface damage and perturbs chemical processes. Thermocouples consist of metals which may be damaged by the harsh chemical environment during wafer processing and also may contribute contaminates to the processing.

Pyrometery offers a direct, noncontact measurement of the emissive radiant power from a surface (black body radiation). However, the emissivity (absorptance) of the surface provides a generally unknown factor and prevents the simple computation of the surface temperature from the emissive radiant power. Indeed, the emissivity of wafer material(s) will depend upon the structure. Typically, wafers will include multiple, somewhat transparent surface layers of various materials.

Hansen et al, 28 Appl. Optics 1885 (1989) measured the emissivity of certain transition metals (which are opaque) by ellipsometry with a HeNe laser source (633 nm) and also measured the radiance at the same wavelength to compute the temperature.

Another approach relies on the temperature dependence of the (complex) dielectric constant of a material and an ellipsometric determination of the dielectric constant to deduce the temperature. Ellipsometry does provide a direct, noncontact measurement, but the weak temperature dependence of the dielectric constant for wafer materials of interest such as silicon implies insufficient accuracy. See Ibrahim et al, 9 J. Vac. Sci. Tech. 1259 (1972) and Tomita et al, 25 Japn. J. Appl. Phys. L925 (1986).

SUMMARY OF THE INVENTION

The present invention provides a direct, noncontact measurement of (layered) wafer temperature by the use of ellipsometry in conjunction with pyrometry. Ellipsometry provides measurement of the optical constants and thicknesses of any layers, and these determine reflectance and transmittance; this, in turn, determines the absorptance which can be used with pyrometry measurements of emissive radiant power at different wavelengths to compute the temperature.

BRIEF DESCRIPTION OF THE DRAWINGS

The drawings are schematic for clarity.

DESCRIPTION OF THE PREFERRED EMBODIMENTS

First Preferred Embodiment Overview

Figure 1:
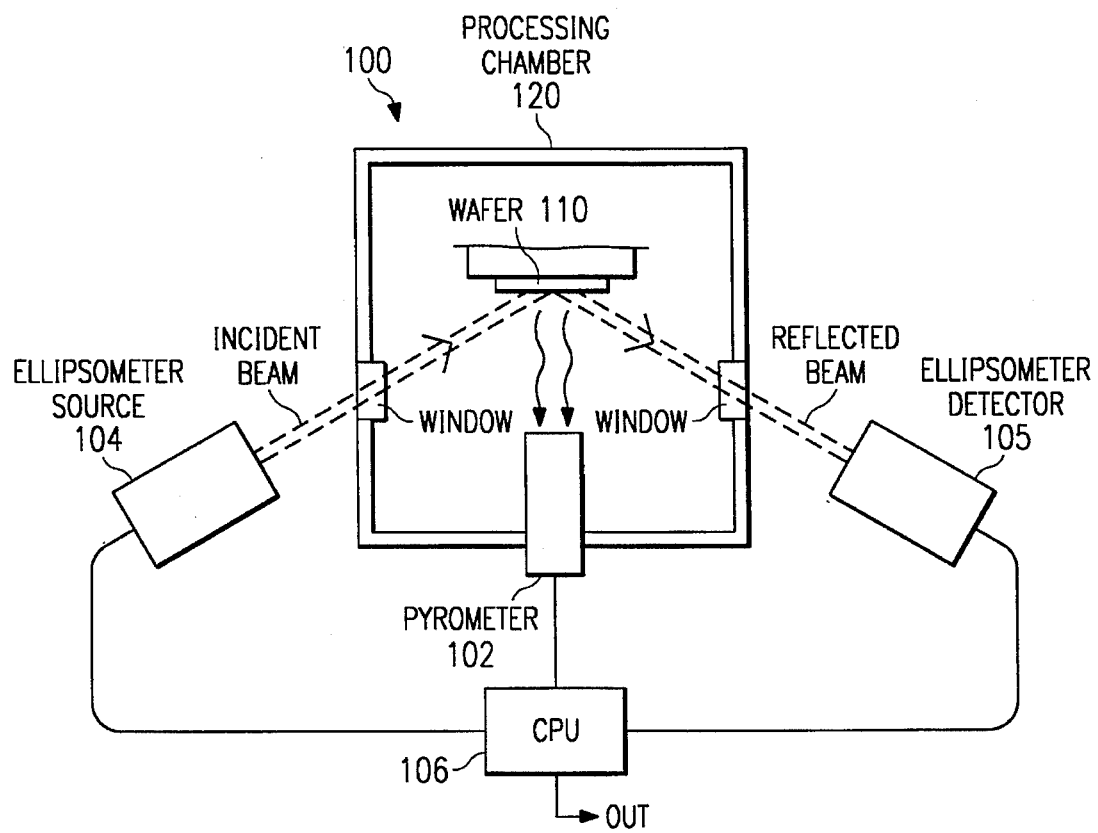
FIG. 1 is a block diagram of a first preferred embodiment temperature sensor.

FIG. 1 heuristically shows first preferred embodiment temperature sensor, generally denoted by reference numeral 100, as including pyrometer 102 and ellipsometer 104–106 both arranged to sample wafer 110 within processing chamber 120. A single controller and computer 106 is shown to control the ellipsometer modulation and detector data acquisition plus compute the temperature output; in fact, separate controllers and computers may be used. Chamber 120 may be a vacuum chamber for carrying out processes such as film deposition, etching, annealing, and so forth on wafer 110. Indeed, chamber 120 may be the growth chamber of a molecular beam epitaxy (MBE) machine. Thus wafer 110 may present a layered surface structure having a surface of at least one layer of known materials and ellipsometer 104–106 will determine a dielectric function which depends upon wavelength and temperature. Ellipsometer 104–106 is a spectroscopic polarization modulated ellipsometer which essentially has a broad incident beam spectrum (e.g., wavelengths from 0.2 μm to 1.05 μm) and a modulated phase shift between the orthogonal components of the incident beam; the detector includes a spectrometer to spread the reflected beam over an array of individual detectors for the various wavelengths. This provides parallel analysis leading to rapid temperature determinations, on the order of 1 second.

Figure 2:
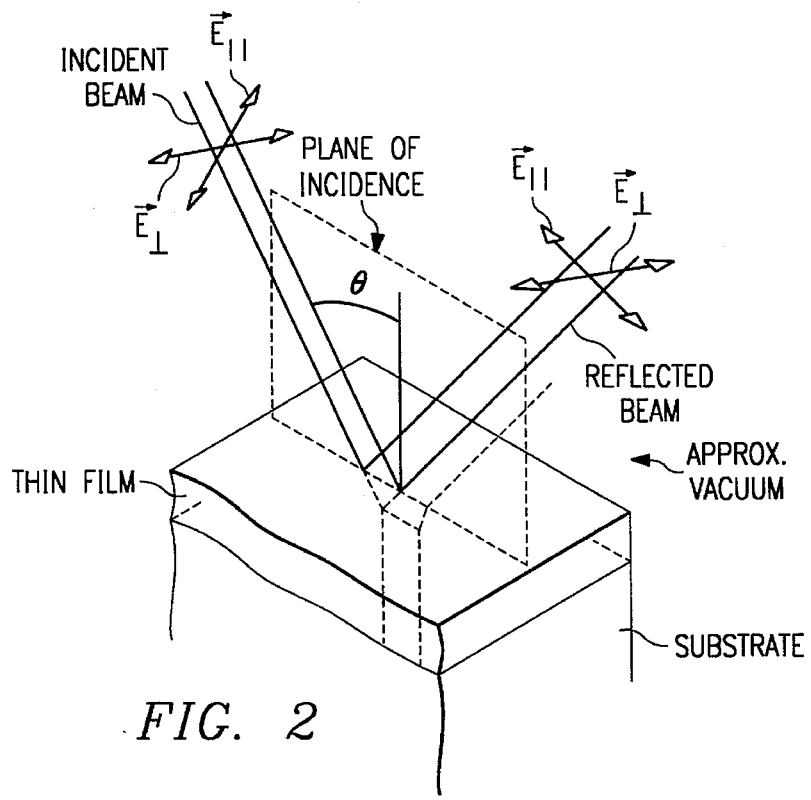
FIG. 2 illustrates the plane of incidence for reflection.

For example, when wafer 110 consists of a single thin film on a uniform substrate as illustrated schematically in FIG. 2, the transmittance at wavelength λ is given by:

$$T(\lambda) = t_{01} t_{12} e^{-i\beta} / [1 + r_{01} r_{12} e^{-i2\beta}]$$

where $r_{01}$ and $r_{12}$ are the Fresnel reflection coefficients for the interfaces from ambient to thin film and from thin film to substrate, respectively, and $t_{01}$ and $t_{12}$ are the Fresnel transmission coefficients of the two interfaces, β is given by:

$$\beta = [\epsilon_1 - \epsilon_0 \sin 2\theta]^{1/2} d_1 / \lambda$$

where $\epsilon_0$ and $\epsilon_1$ are the complex dielectric constants (dependent on both wavelength and temperature) of the ambient and the thin film, respectively, $d_1$ is the thickness of the thin film, and θ is the angle of incidence. The angle of incidence is fixed by the apparatus setup. Of course, the complex dielectric constant e is just the square of n–ik where n is the index of refraction and k is the extinction coefficient. Similarly, the reflectance is given by $$R(\lambda) = 1 + r_{12} e^{-i\beta} / [1 + r_{01} r_{12} e^{-i2\beta}]$$

Thin film and substrate materials (e.g., silicon oxide and silicon or AlGaAs and GaAs) would be generally known during processing and thus their optical constants also known as functions of temperature and wavelength; however, the thin film thickness is unknown and significantly affects the transmittance and reflectance as may be seen in the expression for β. Note that thin films in semiconductor processing typically have thicknesses on the order of roughly 0.01 to 1 μm.

Ellipsometer 104–106, described in the following section, determines film thickness (and the optical constants) by analysis of the reflected beam polarization for wavelengths in a range such as from 0.4 μm to 0.85 μm (near ultraviolet to near infrared). Then knowledge of the thin film thickness permits computation of $T(\lambda)$ and $R(\lambda)$ by the above equations. Note that the wavelength X of interest would be the center of the bandpass filter of pyrometer 102 at wavelengths $\lambda, \lambda_2 \ldots \lambda_N$ with $N \geq 2$ and would typically be taken near the blackbody radiation maximum for the wafer temperature; that is, $\lambda$ would typically be in the range of 1 μm to 5 μm.

By conservation of energy, the absorptance $A(\lambda)$ equals $1-T(\lambda)-R(\lambda)$. Thus temperature sensor 100 effectively uses ellipsometer 104–106 to find the absorptance of wafer 110 at the temperature of wafer 110 and for the wavelengths of interest for pyrometer 102.

The emissive power is given by:

$$F(\lambda)=A(\lambda)2\pi hc^3/\lambda^5[e^{hc/\lambda kT}-1]$$

where h is Planck's constant, c is the speed of light in vacuum, k is Boltzmann's constant, and T is absolute temperature. Pyrometer 102 accurately measures $F(\lambda)$, so all of the terms in the equation are known except T, and CPU 106 can solve the equation to find an accurate T. Indeed, pyrometers typically operate with a selectable wavelength filter, and an emissivity correction (equal to $A(\lambda)$ for a filter centered at $\lambda$) may be fed into pyrometer 102 as an analog voltage derived from a digital-to-analog conversion of a digital $A(\lambda)$ output of CPU 106.

The rapid temperature determination by temperature sensor 100 permits temperature monitoring during wafer processing.

Ellipsometer

Figure 3:
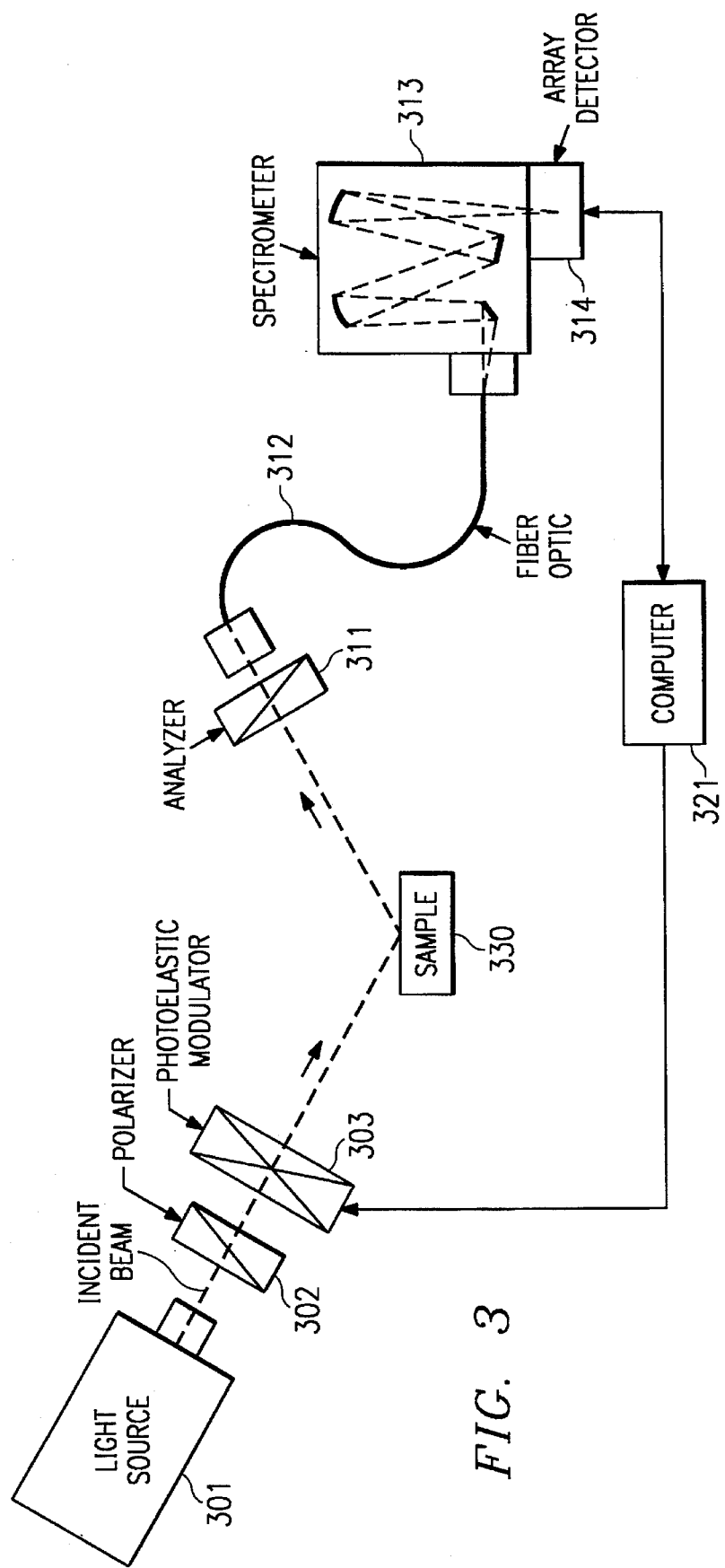
FIG. 3 shows a polarization modulation ellipsometer.

FIG. 3 diagrammatically shows ellipsometer 104–106 including broad spectrum light source 301, linear polarizer 302, photoelastic modulator 303, analyzer polarizer 311, fiber optic cable 312, spectrometer 313, array detector 314, and controller computer 321. This corresponds to FIG. 1 with ellipsometer source 104 including light source 301, polarizer 302, and modulator 303, and ellipsometer detector 105 including analyzer 311, cable 312, spectrometer 313, and array detector 314.

Ellipsometer 104–106 operates as follows. Light source 301 may be a 100 watt xenon arc lamp and provides sufficient radiant energy for wavelengths from 0.2 μm to 1.05 μm. This light is collimated with lenses and shutters to form a broad spectrum incident beam. Polarizer 302 plane polarizes the incident beam, for example, with a polarization angle of ±45° with respect to the plane of incidence. The plane of incidence is the plane defined by the incident and reflected beams and the perpendicular to sample surface 330. FIG. 2 illustrates the plane of incidence and shows the incident beam electric field components $E_\parallel$ and $E_\perp$ which are parallel and perpendicular to the plane of incidence, respectively, and in phase for plane polarization. Polarization of ±45° with respect to the plane of incidence just means that $E_\parallel$ and $E_\perp$ have equal magnitudes.

Photoelastic modulator 303 may be a block of isotropic fused quartz which has an applied sinusoidal uniaxial strain that causes the phase velocity of the electric field component along the strain axis to vary in a periodic manner. Typically, the strain axis is taken parallel or perpendicular to the plane of incidence for the case of the incident beam plane polarized at ±45°. A piezoelectric transducer affixed to the fused quartz can induce the sinusoidal strain. In FIG. 3 computer 321 provides a 50 KHz signal to drive modulator 303. With the strain axis perpendicular to the plane of incidence, the phase of $E_\perp$ will differ from that of $E_\parallel$ sinusoidally, and the incident beam now has a modulated polarization. Indeed, a linear polarizer analyzer with polarization parallel to that of polarizer 302 and with polarization strength K would transmit an intensity proportional to $1+K\cos(\delta(t))$ where $\delta(t)$ is the phase difference of $E_\parallel$ and $E_\perp$. Similarly, a circular polarizer analyzer would transmit an intensity proportional to $1+K\sin(\delta(t))$. In effect, the polarization modulation simplifies analysis of the eventually detected reflected beam due to the ability to separately measure the intensities of the zeroth, first, and second harmonics of the modulation frequency and thereby provide two independent equations for the two ellipsometric angles.

The modulated incident beam reflects from surface 330 with the $E_\parallel$ and $E_\perp$ components having differing reflectances which depend upon the angle of incidence and the sample structure and materials. The phase shift of reflected $E_\parallel$ relative to reflected $E_\perp$ due to the reflection is denoted by $\Delta$, and the ratio of magnitudes of reflected $E_\parallel$ to reflected $E_\perp$ is denoted by $\tan\Psi$ for the case of the ratio of magnitudes of incident $E_\parallel$ to incident $E_{195}$ equal to 1 (as is the case for the ±45° initial polarization). That is, $\Psi$ would be the angle of polarization of the reflected beam if it were plane polarized. $\Delta$ and $\Psi$ are the ellipsometric angles, and $\tan\Psi e^{i\Delta}$ equals the ratio of the parallel and perpendicular (complex) reflectances of surface 330.

Analyzer polarizer 311 is a linear polarizer and typically would also have a polarization angle of ±45° with respect to the plane of incidence to simplify the harmonic intensity expressions. Indeed, with $\delta(t)=M\sin(\omega t)$, to first order approximation the zeroth (dc), first ($\omega$), and second ($2\omega$) harmonic intensities exiting analyzer 311 are, respectively, $$S_0=C[1+J_0(M)\sin2\Psi\cos\Delta]$$

$$S_1=C2J_1(M)\sin2\Psi\sin\Delta$$

$$S_2=C2J_2(M)\sin2\Psi\cos\Delta$$

where C is a constant of proportionality and $J_i(M)$ is the ith Bessel function at M. Of course, $\Psi$ and $\Delta$ depend upon $\lambda$, and M is inversely proportional to $\lambda$ and directly proportional to the exciting voltage of the piezoelectric transducer in modulator 303.

Spectrometer 313 spreads out the reflected beam according to wavelength over detector array 314 which is a linear array of 46 silicon photodiodes operating at room temperature and roughly 5 cm in length. Each photodiode receives a band of wavelengths, e.g., 0.55 μm to 0.56 μm, and generates a current in proportion to the received intensity. Of course, the received intensity fluctuates due to the polarization modulation at frequencies of dc, 50 KHz, and 100 KHz (i.e., $S_0$, $S_1$, $S_2$), and also at higher harmonics. The current from each photodiode is sampled with a sampling rate of 1 MHz for an interval of 20 microseconds by a sampling analog-to-digital converter; 20 microseconds is one period for the modulation frequency of 50 KHz. Computer 321 Fourier transforms each 20 microsecond sampling using an FFT procedure to extract $S_0$, $S_1$, and $S_2$. A multiplexer sequentially selects the photodiodes for sampling, and the piezoelectric transducer excitation voltage is adjusted for each sampling to keep M equal to about 2.405, which is the first zero of $J_0$, and thus simply determine C as the dc detected signal. The photodiode modulator may adjust the magnitude of the phase difference between components of the input beam in response to the selection of the one of photodiodes being sampled. The other two equations then determine $\Psi$ and $\Delta$. Note that the 2.405 first zero of $J_0$ frequently is expressed as 137.62 degrees.

Alternative arrangements, such as not varying M to make the $J_0$ term vanish, would simplify the control of modulator 303 but add some complexity to the equation solution. Also, greater speed could be achieved by providing a sampling analog-to-digital converter for each of the photodiodes for simultaneously sampling.

Each wavelength yields two equations for unknowns, so a multilayer wafer structure with many unknown layer thicknesses would require several wavelengths' information. Further some wavelengths may provide no information for certain wafer structures, such as when a layer is a quarter wavelength thick and provides no reflection. Consequently, temperature sensor 100 uses ellipsometer 104–106 having detector array 314 with more than just a few detectors.

To deduce layer thicknesses $d_1$ and the complex dielectric constants $\epsilon_j$ (functions of $\lambda$) of a layered wafer 110, a model of the layering must be employed. The continuity of the tangential components of the electric and magnetic fields and the normal components of the electric displacement and the magnetic induction fields at an interface provide equations for the layer thicknesses and dielectric constants involving the angle of incidence. Numerical solution then yields the layer thicknesses and dielectric constants which take into account its temperature. Then the reflectance and transmissivity may be computed, and the absorptance deduced for wafer 110. Note that the model of the layering typically presumes knowledge of the layer materials, so determination of thicknesses at wavelengths used by ellipsometer 104–106 then permits computation of absorptance at the wavelength used by pyrometer 102.

Pyrometer

Pyrometer 102 is just an infrared photodiode made of a material such as indium antimonide (InSb) or mercury cadmium telluride ($Hg_{1-x}Cd_xTe$) situated within a cryogenic cooler and with a bandpass filter to select wavelengths in a narrow band near the blackbody radiation maximum for the expected wafer temperature. The bandpass filter could be a notch filter made of a stack of dielectrics and relying on interference effects. Pyrometer 102 just measures the total radiant power received within its filter's band of frequencies (the quantum efficiency of absorption is relatively constant across the band), and calibration with blackbodies at known temperatures gives a reference for comparison. Thus once the multiplicative factor of absorptance for the band of frequencies is known, the temperature can be determined.

Modifications and Advantages

The preferred embodiments may be varied in many ways while retaining one or more of the features of pyrometer with compensation for absorptance made by an essentially simultaneous, independent measurement of absorptance at different wavelengths, such as from ellipsometry.

For example, the ellipsometer could be a rotating analyzer, rotating polarizer, rotating analyzer or static component instrument such as the division of amplitude photopolarimeter of Azzem, 29 Opt. Acta 685 (1982). The pyrometer could consist of any infrared or near infrared sensitive material with a method for selecting or determining wavelength, including uncooled infrared detectors based on ferroelectrics.

The use of multiple wavelength analysis for determination of absorptance has the advantage of applicability to layered structures, as found in semiconductor processing, and thus combination with pyrometry to provide direct, noncontact temperature measurement.

The present invention includes an ellipsometer measurement system including an energy source for generating an electromagnetic wave, a polarizer for receiving and polarizing the electromagnetic wave, a phase modulator for modulating the phase of the electromagnetic wave, an electromagnetic wave to impinge the sample to be measured, a phase modulator for modulating the phase of the electromagnetic wave, the electromagnetic wave to impinge a sample to be measured, an analyzer to receive a reflected wave from the sample and select a given polarization angle, a spectrometer for separating the reflected wave into a plurality of substantially monochromatic waves, an array detector for detecting an intensity at a phase of each of the monochromatic waves, the array detector including a separate detector for each of the monochromatic waves, and circuitry for analyzing the detected intensity and phase to determine selected information about the sample.

Additionally, the present invention includes a temperature sensor wherein the analyzing circuitry calculates the selected information about a characteristic of the sample based the detected intensity and phase.

What is claimed is:

1. A temperature sensor for a layered structure, comprising:

a pyrometer; and an absorptance detector coupled to said pyrometer, said detector determining emissivity of a layered structure based on layer thickness measurements;

wherein said absorptance detector provides an emissivity correction for said layered structure to said pyrometer.

2. The temperature sensor of claim 1, wherein:

said absorptance detector includes an ellipsometer with plural wavelength sensitivity.

3. The temperature sensor of claim 2, wherein:

said ellipsometer includes a broad spectrum input beam source, a spectrometer, and an array of photodetectors, whereby plural wavelengths may be simultaneously sensed.

4. The temperature sensor of claim 3, wherein:

said ellipsometer includes a photoelastic modulator in said input beam source.

5. The temperature sensor of claim 4, wherein:

ones of said photodetectors are sequentially sampled; and said photoelastic modulator adjusts the magnitude of the phase difference between components of an input beam in response to the selection of the one of said photodetectors being sampled.

6. The temperature sensor of claim 5, wherein:

said ones of said photodetectors are sampled at a rate of about 1 MHz and for a time interval of about 20 microseconds for each photodetector; and said photoelastic modulator modulates the phase difference between components of an input beam at a frequency of about 50 KHz.

7. The temperature sensor of claim 2, wherein:

said pyrometer measures emissive power about a wavelength which is longer than the wavelengths used by said ellipsometer.

8. The temperature sensor of claim 1, wherein:

said absorptance detector includes an ellipsometer and a computer, said computer programmed with relations between layer thicknesses and ellipsometric variables.

9. A temperature sensor, comprising:

a pyrometer with a passband filter centered at wavelength $\lambda_0$;

an ellipsometer with detection bands centered at wavelengths $\lambda_1, \lambda_2, \ldots \lambda_N$, with $N \geq 2$; and a controller with inputs coupled to outputs of said pyrometer and said ellipsometer and outputting a temperature, said controller programmable to compute absorptance based on layer thickness measurement outputs of said ellipsometer and apply the absorptance as a correction to the output of said pyrometer.

10. The temperature sensor of claim 9, wherein:

$\lambda_0$ is greater than $\lambda_1, \lambda_2, \ldots \lambda_N$.

11. The temperature sensor of claim 9, wherein:

said ellipsometer includes a phase difference modulation for an incident beam.

12. A temperature sensor as in claim 9, wherein said ellipsometer comprises:

an energy source for generating an electromagnetic wave;

a polarizer for receiving and polarizing the electromagnetic wave;

a phase modulator for modulating the phase of the electromagnetic wave;

the electromagnetic wave to impinge a sample to be measured;

an analyzer to receive a reflected wave from the sample and select a given polarization angle;

a spectrometer for separating the reflected wave into a plurality of substantially monochromatic waves;

an array detector for detecting an intensity and phase of each of the monochromatic waves, said array detector including a separate detector for each of the monochromatic waves; and circuitry for analyzing the detected intensity and phase to determine information about the sample.

13. A temperature sensor as in claim 12, wherein said analyzing circuitry determines said information about a characteristic of said sample based on said detected intensity and phase.

14. A method of temperature sensing of a non-metal layered structure, comprising the steps off:

determining the absorptance of a non-metal layered structure by ellipsometry based on layer thickness measurements with said non-metal layered structure including at a surface at least one layer of known materials;

determining an emissive power at said surface of said non-metal layered structure by pyrometry; and computing the temperature from said emissive power and said absorptance.

15. The method of claim 14, wherein:

said steps of determining the absorptance, determining the emissive power, and computing the temperature are repeated at a rate of roughly once per second.

* * * * *